United States Patent [19]

Comparetto

[11] Patent Number: 4,502,474
[45] Date of Patent: Mar. 5, 1985

[54] BONE WEDGE GUIDANCE SYSTEM

[76] Inventor: John E. Comparetto, P.O. Box 433, Nassawadox, Va. 23413

[21] Appl. No.: 425,574

[22] Filed: Sep. 28, 1982

Related U.S. Application Data

[63] Continuation-in-part of Ser. No. 294,653, Aug. 20, 1981, and a continuation-in-part of Ser. No. 127,010, Mar. 4, 1980, abandoned.

[51] Int. Cl.³ .............................................. A61F 5/04
[52] U.S. Cl. ................................. 128/92 H; 128/92 E
[58] Field of Search ............... 128/92 R, 92 E, 92 EB, 128/303 R, 305, 317

[56] References Cited

U.S. PATENT DOCUMENTS

| | | | |
|---|---|---|---|
| 4,150,675 | 4/1979 | Comparetto | 128/92 E |
| 4,337,773 | 7/1982 | Raftopoulos et al. | 128/305 |
| 4,347,845 | 10/1982 | Mayfield | 128/303 R |
| 4,349,058 | 9/1982 | Comparetto | 128/92 E |

OTHER PUBLICATIONS

J. E. Comparetto, "The Osteoguide System" Brochure, No Date.

Primary Examiner—C. Fred Rosenbaum
Assistant Examiner—C. W. Shedd
Attorney, Agent, or Firm—Shoemaker and Mattare, Ltd.

[57] ABSTRACT

A wedge guide system of variable but precise angular dimensions that allows the excision of a precise bony wedge by the alternate use of arcuate (crescentic) and planar saws in a stable and accurate manner. Right and left sided wedges can be taken. The precise wedge can be angulated in respect to the long axis of the bone by a directional guide structure that complies with data for each surgical case enabling the surgeon to make triplanar bone corrections.

16 Claims, 33 Drawing Figures

BONE WEDGE GUIDANCE SYSTEM

This patent application is a continuation-in-part of Ser. No. 294,653, filed Aug. 20, 1981, entitled Bone Wedge Guidance System, and the previously abandoned application Ser. No. 127,010, entitled Matrix Guide For A Precise Wedge Osteotomy.

BACKGROUND OF THE INVENTION

Field of the Invention

The guide apparati and processes herein are additional and improved embodiments of the bone-cut guide of the parent applications and its application in surgery.

OBJECTS OF THE INVENTION

An object of the present invention is to provide various lock and key structures for positioning guide slot arm of a guide with respect to a curved cut as made in a bone.

Another object of the invention is to provide a peg and hole structure for positioning the guide slot arm of the guide in relation to a curved cut as made in a bone.

Another further object of the invention is to provide a guide device with a double arm slot guidance structure for use in the formation of a replaceable wedge osteotomy.

Another still further object of the invention is to provide a reversible bone-cut guide capable of yielding right or left bone wedges regardless of the orientation of the curved or arcuate cut.

Another object of the invention is to provide a guide with a curved or slanted surface to accommodate the cylindrical curvature of some bones.

Another object of the invention is to provide a reversible bone-cut guide that is adjustable and is read by scalar means.

Another object of the invention is to provide a guide holder for the surgical assistant.

Another object of the invention is to provide a guide device to allow an arcuate cut of 180 degrees or more.

A further object of the invention is to provide a method of positioning the initial osteotomy cut to move the bone in space to a predetermined position.

Other objects will become apparent to one skilled in the art after reading the following description and specification.

DETAILED DESCRIPTION OF THE INVENTION

Figure 1:
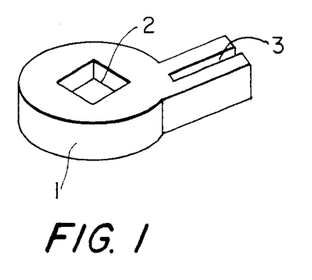
FIG. 1 is a perspective view of the upper section body and guide slot arm of a first embodiment of a lock and key osteoguide.

FIG. 1 depicts the upper body (1) of the first embodiment of the osteoguide having a square-shaped recess (2) in body portion (1). Guide slot arm (3) comes off body portion (1) at a specific angulation to the recess (2). Recess (2) is cut or formed into body (1) at different positional angular variations to the guide slot arm starting from one degree from the end of the arcuate tab (5) of the lower section to any suitable degree of the arcuate tab (5) in any number of suitable increments. Recessed portion (2) fits over square projection (4) of FIG. 2 which is attached to the curved tab (5) of the lower section of the lock and key osteoguide. Square projection (4) is stationary with respect to the arcuate tab. The positional variations of the upper portion of the osteoguide lock and key apparatus is dictated by the positional relationship of the recessed portion (2). The opposite situation can be employed when the recessed portion (2) is kept constant while the projection (4) is varied positionally relative to the curved tab (5). From the standpoint of easiest fabrication the first embodiment with a varying recessed portion (2) is preferred. It is envisioned that the square lock and key conformation can take any suitable shape, such as an oval, triangle, key hole, trapezoid or any polygon, or irregular shape as long as the recess (2) and projection (4) fit one into the other with no "play" or movement. The recess to projection position can be varied in fabrication to effect an angular change of the guide slot arm to the arcuate tab.

Figure 3:
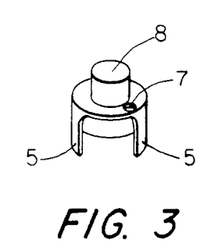
FIG. 3 is a perspective view of the curved tab lower section of a peg and hole second embodiment osteoguide.
Figure 4:
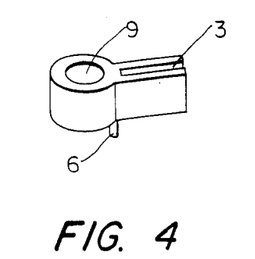
FIG. 4 is a perspective view of the guide slot arm and cylindrical body of a peg and hole second embodiment osteoguide.

Another example of incremental osteoguide guide slot arm positional changing can be seen in the second embodiment of FIGS. (3) and (4) where guide arm (3) rests on lower curved tab section (5) as post (8) inserts in hole (9) and is turned until peg (6) of the guide slot arm inserts into peg hole (7). The peg slot arm, the peg hole, or the post can be moved incrementally in fabrication to effect a degree change of the guide slot arm along the arcuate tab to effect a different planar cut of bone. For ease of fabrication of this second embodiment, the incrementally varied peg hole with stationary peg would be the osteoguide of choice.

Figure 7:
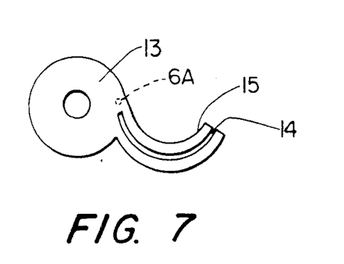
FIG. 7 is a plan view from above of a curved arm with curved guide slot osteoguide.
Figure 8:
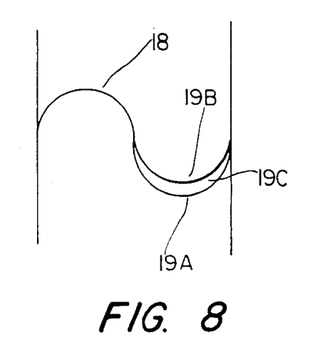
FIG. 8 is an example in schematic form of an osteotomy performed by the curved arm osteoguide of FIG. 7.

Another third embodiment of the osteoguide is seen in FIG. 7, consisting of an upper body arm (15) with curved slot (14) coming off body (13) at the level of peg (6A). A curved cut (18) is made, see FIG. 8, with an arcuate oscillating blade all the way through the bone. Then the one degree curved tab section or angle locator (5) is selected and combined with the upper body section (13) by means of peg (6A) and hole (7) of the curved lab locator as seen in FIG. 3. The curved slot (14) is thus aligned on the curved cut (18) to make a curved partial cut (19A) into the bone with an arcuate saw blade. The desired degree wedge is then made by selecting a second curved tab degree locator (5) of the precise degree needed. It is attached to the upper body portion (13) in the manner previously described. The arcuate cut (19B) is then made entirely through the bone with an arcuate saw blade. The partial cut (19A) is now completed entirely through the bone thus yielding wedge (19C). The bone correction is now accomplished by rotating the bony parts over the curved cut (18) thus closing the void made by the removal of the curved wedge (19C).

Figure 9:
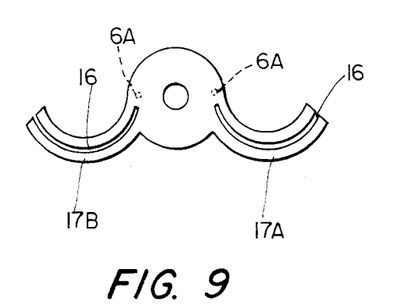
FIG. 9 is a plan view from above of a double curved arm with curved guide slot osteoguide.

In FIG. 9, another fourth embodiment with an upper body having double curved slot arms 17A, 17B is shown. The double slots 16 are utilized to make double curved cuts in a bone and to fabricate a curved wedge that is removed from one side of the bone and then replaced into the void made by the closure of the space it vacated.

Figure 2:
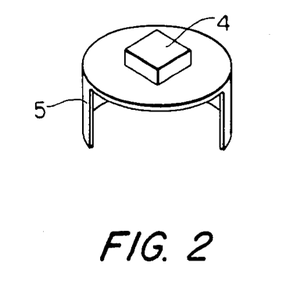
FIG. 2 is a perspective view of the lower curved tab section of the first embodiment of a lock and key osteoguide.
Figure 10:
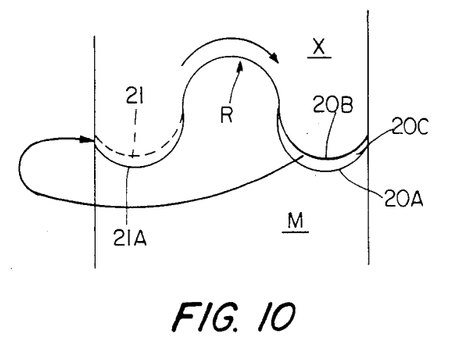
FIG. 10 is an example in schematic form of an osteotomy using the double curved arm osteoguide of FIG. 9; it also depicts wedge reversal.

First, curved cut (R), FIG. 10, is made entirely through the bone. Then, a partial curved cut (20A) is made with the curved guide arm (17A). The desired wedge to effect an angular change in the bone is ascertained by the surgeon and the appropriate curved tab locator (5) as seen in FIGS. 2 and 3, is selected for the formation of curved cut (20B) which is made entirely through the bone. Partial cut (20A) is then completed yielding curved wedge (20C). Curved wedge (20C) is removed, rotated 180 degrees in the surgeon's hands, and then replaced in the duplicate void made by the rotation of bone parts (X) and (M) over curved cut (R). The curved cut (21A) is made by twin guide arm (17B) when the curved tab angle locator is in position for cut (20B). The foregoing wedge replacement method had been previously described in patent application Ser. No. 32,309: *Cutting Tool And Method Of Using Same* now U.S. Pat. No. 4,349,058.

Figure 11:
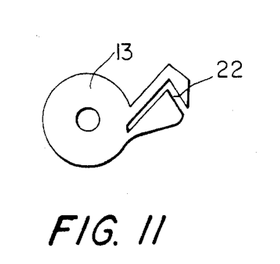
FIG. 11 is an example of an acute angle accordian-shaped slot and arm osteoguide.
Figure 12A:
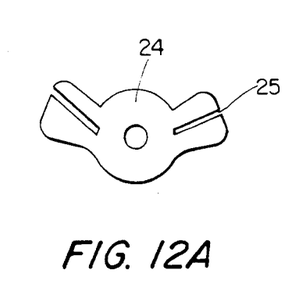
FIG. 12A is an example of a planar slot double armed osteoguide.
Figure 12B:
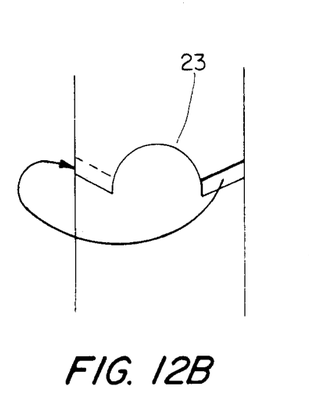
FIG. 12B is an example in schematic form of an osteotomy effected by use of a double armed planar slot osteoguide, of FIG. 12A.

It should be noted that the osteoguide arms in FIGS. (7) and (9) could have other configurations, such as an accordian shape (22), shown in FIG. 11. The double arm osteoguide (24), shown in FIG. 12A, could have double planar slots (25) for making a double curved-vee osteotomy (23), as depicted schematically in FIG. 12B.

Figure 13:
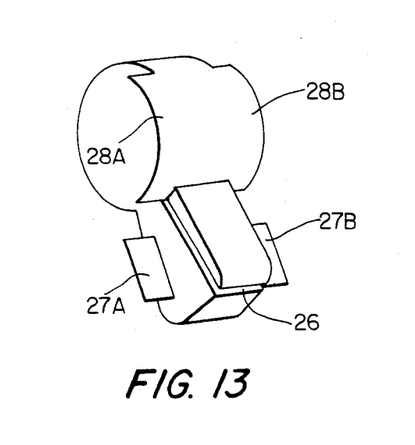
FIG. 13 is a perspective view of a reversible bone-cut guide.
Figure 14:
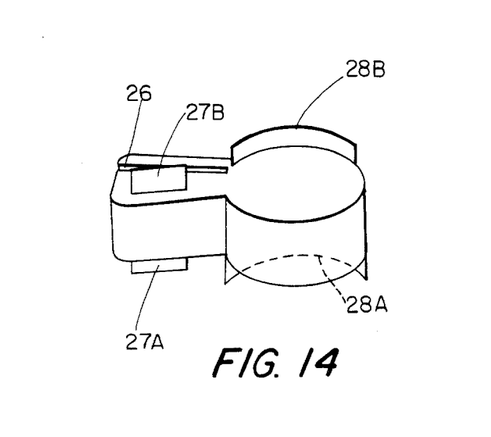
FIG. 14 is another perspective view of the bone-cut guide of FIG. 13.
Figure 15:
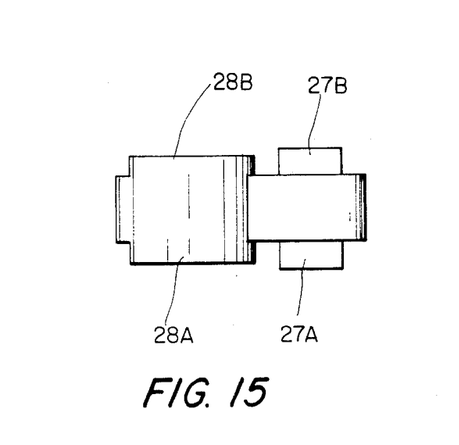
FIG. 15 is still another view in elevation of the bone-cut guide of FIG. 13.
Figure 16:
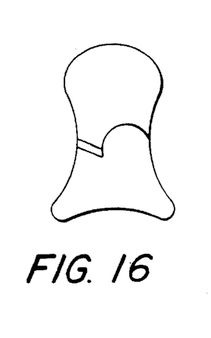
FIGS. 16, 17, 18, and 19 show in schematic form the variation of osteotomy orientation effected by a reversible guide.
Figure 17:
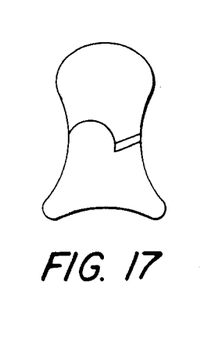
Figure 18:
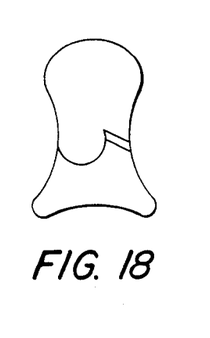
Figure 19:
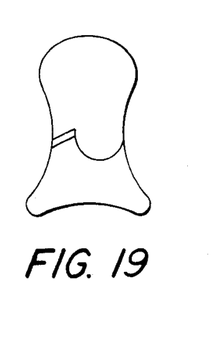

Another embodiment of the invention, a reversible guide, can be seen in FIGS. 13, 14, and 15. Common slot (26) is used in conjunction with curved extension (28A) and straight tab lock (27A) for making left-sided straight cuts from distally oriented apex arcuate as depicted in cuts, FIG. 16; while curved extension (28B) and straight tab lock (27B) are used in making right-side straight cuts from distally oriented apex arcuate cuts, as depicted in FIG. 17. If the apex of the arcuate cuts are reversed or proximal, then (27A and 28A) would be used in making right-sided cuts, as depicted in FIG. 18; while (27B and 28B) would be used in making left-sided cuts, as depicted in FIG. 19.

Figure 31:
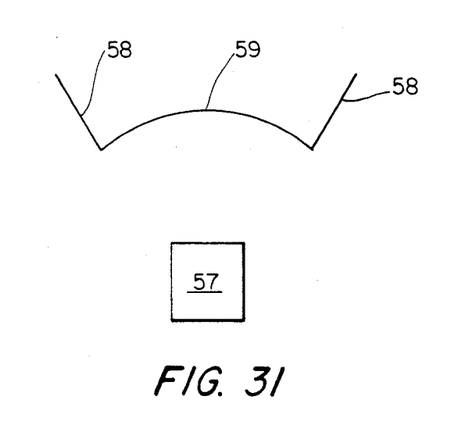
FIGS. 31 and 32 are schematic views of a reversible guide cut.
Figure 32:
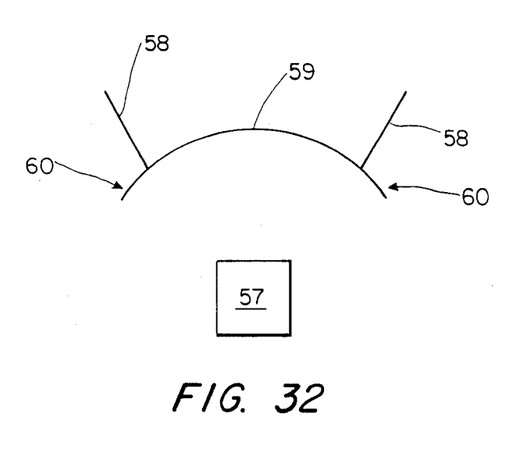

FIGS. 31 and 32 show as schematic views the surgical cuts made by such a reversible guide. In FIG. 31, the right and left slot positions (58) for 0° remains on the same points of the curved flange (59) as directed by attachment (57). FIG. 32 indicates right and left slot positions for the subsequent X° cut. Sections (60) are radial extensions of curved flange (59) in order to locate slot (58) X° from the 0° cut. Note that slot (58) is on the same point of the curve (left and right) in both FIG. 31 and FIG. 32. In short, the increased curved flange length positions the slot a precise number of degrees away from the first straight (0°) cut.

Figure 20:
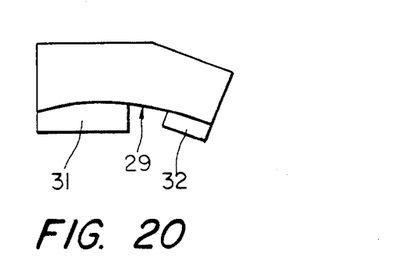
FIG. 20 is a cross-sectional view through a curved bottom bone-cut guide.

FIG. 20 shows a curved bottom (29) guide from which a curved tab extension (31) and a straight tab lock (32) are attached. This embodiment might be helpful in the few instances where the bone surface curves dramatically. In surgeries already performed using the guides, this curvature was not needed.

Figure 21:
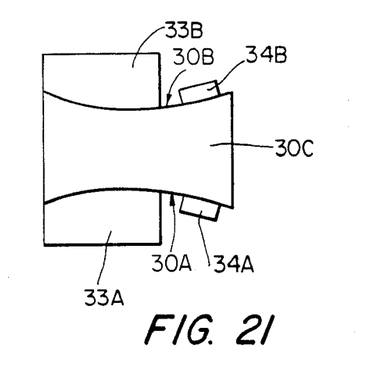
FIG. 21 is a cross-sectional view showing a reversible bone guide with curved-to-the-bone surfaces.

FIG. 21 shows curved surfaces (30A and 30B) of slot back (30C) pitching to accommodate bone curvature in a reversible type guide such as described in FIGS. 13, 14, and 15. Each curved surface has curved tab extensions (33A and 33B) and straight tab lock extensions (34A and 34B).

Slot (26) comes very close to tab lock (27A and 27B) when fabricating small degree guides, making welding or casting of the tab tedious. The closer the straight tab lock is located to the end of the curved tab, the better it inserts into the first straight bone cut. This is especially true in the situation where the bone curve drops abruptly away.

Figure 27:
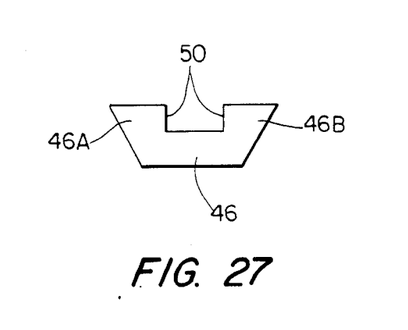
FIG. 27 is a view of a trapezoidal shaped tab lock insert.
Figure 28:
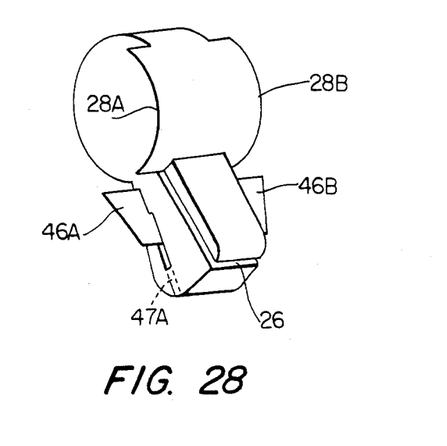
FIG. 28 is a perspective view of a guide with the tab lock insert of FIG. 27 therewith.
Figure 29:
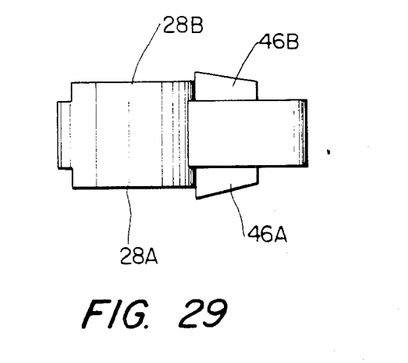
FIG. 29 is a side elevational view of a guide with tab lock insert.

A removable (as an insert) or stationarily affixed trapezoidal shaped straight tab lock (46) of FIG. 27 fits into slot (47) of the reversible guide of FIG. 28. The trapezoidal shape and cut-out (50) allow for an easy insertion. In machining slot (47), it might be easier to extend slot (47) through area (47A). Cut-out (50) allows the tab lock (46) to extend wings (46A and 46B) closer to the end of the curved tab extensions (28A and 28B, respectively). The need for cut-out (50) is further understood when it is noted that slot (47) cannot be fabricated close to the curved tab extension in small degree guides without slot (47) running so close to slot (26) that the wall between them is structurally thin and weak; thus slot (47) can be kept a safe distance from the curved tab extension and slot (26) while the tab extends inwardly to the curved tab extension as allowed by the cut-out (50).

Figure 30:
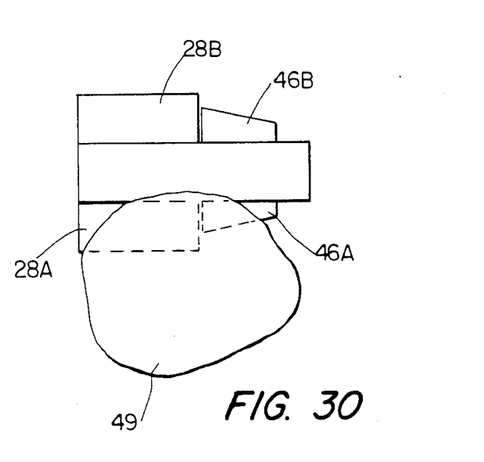
FIG. 30 is a cross-sectional view of a tab lock guide of FIGS. 27–29 in a bone.

The trapezoidal shape enhances visualization of the seating of the guide without sacrificing depth of the tab lock penetration into the first straight cut of bone. The trapezoidal tab lock inserts can come in various sizes to fit different size guides as well as different bone configurations. The trapezoidal tab lock can be inserted in slot (47) during surgery, after the curved tab extension of the guide has already been seated and positioned in the arcuate bone cut. FIG. 30 shows the trapezoidal lock inserted into bone (49) with an abruptly falling away bone surface.

Figure 22:
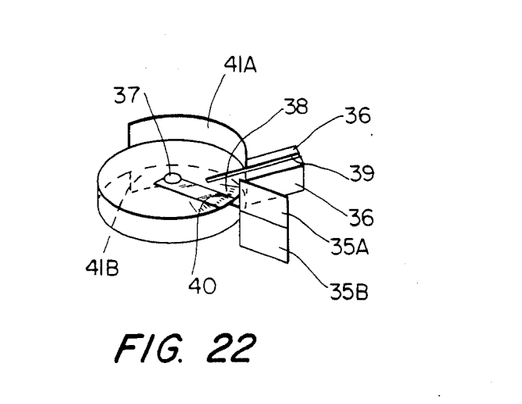
FIG. 22 shows an adjustable reversible guide in perspective view.

Another embodiment, FIG. 22, includes an adjustable guide where the straight tab lock (35B) connected to pivot arm (40) is inserted in the first partial cut of bone which has been made at the internal end of the arcuate cut via slot means (39). The slot block (36) is rotated on the axis of pivot member (40) (from the last position) until slot (39) is a prescribed number of degrees away from the straight tab lock (35B), and consequently the first partial straight cut, at which point it is tightened in position by any convenient fixation means such as a screw (37). The slot (39) is now used to make the second straight cut all the way through the bone. The partial straight cut is now finished yielding the wedge. The prescribed number of degrees for the slot's second positioning, described above, is visualized on a scale means (38) on the guide surface.

Figure 23:
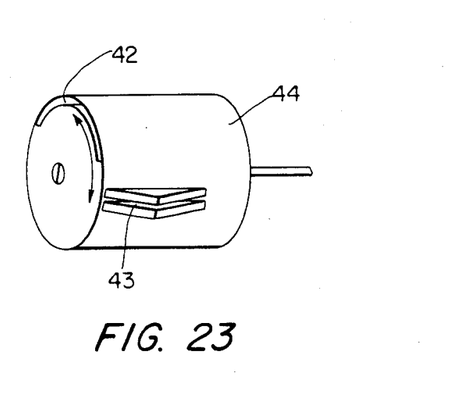
FIG. 23 is a perspective view of a rheostat scalar means.

Another method of visualization of the number of degrees moved by slot (39) from straight tab lock (35B) would be the use of a rheostat apparatus (44) of FIG. 23 and a microcomputer with digital display. Curved slot (42) fits over curved extension (41A) of FIG. 22 while straight slot (43) fits over straight lock tab (35A); extensions (41B and 35B) are in their respective bone cuts. As the slot (39) is rotated around the axis of pivot member (40) to its prescribed angular position, the curved extension (41A) rotates slot means (42) of rheostat (44) the same distance away from its slot (43) changing an electrical resistance. The change is expressed in degree increments on an electronic digital display computer screen as the slot (39) is rotated to the desired angular repositioning. The preference of such a screen display is apparent when considering the degree of difficulty that has been experienced in reading scalar means on guide prototypes.

Figure 24:
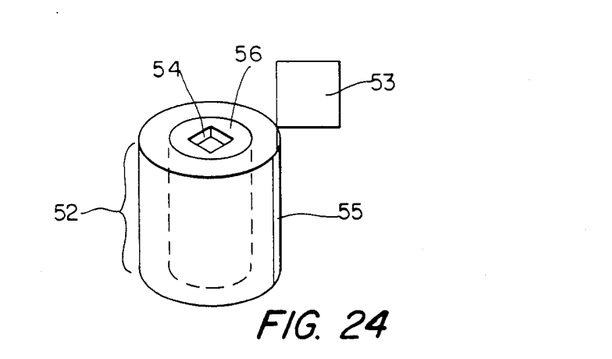
FIGS. 24 and 25 illustrate another embodiment of a rheostat apparatus.
Figure 25:
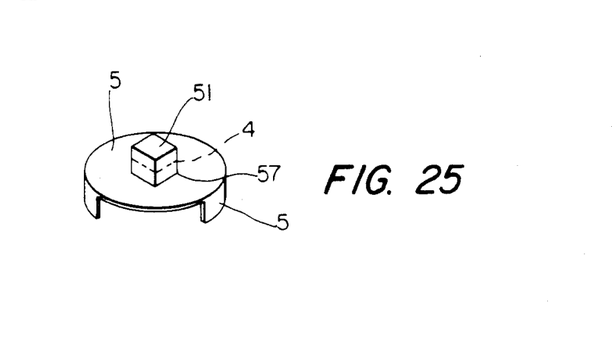

Another embodiment of a rheostat apparatus can be seen in FIGS. 24 and 25. Extension flange (53) is firmly attached on part of the outer shell (55) of rheostat (52). Recess (54), in rotatable, movable inner core (56), FIG. 24, accepts section (51) of elongated section (4) of curved lock section (5), while section (57) of curved section (5), FIG. 25, accepts guide slot arm (3). Extension (53) inserts into the slot of guide arm (3); guide arm (3) is rotated from one degree after a straight cut has been made to the degree number desired for a second cut. Extension flange (53) rotates with the guide arm, while the curved tab section remains stationary with the rheostat inner core. The variation of electrical resistance can be measured as described previously.

Figure 26:
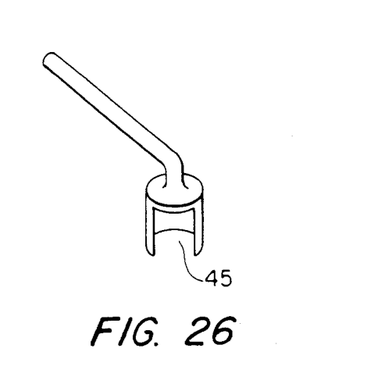
FIG. 26 is a perspective view of a guide holder.

FIG. 26 is an example of a guide holder which enables the surgical assistant's hand to be out of the operative site. Opening (45) allows the guide slot block to extend out of the holder. The holder rotates the edge of opening (45) against the guide slot block to rotate the curved tab extension (41B) to the internal end of the arcuate in the bone cut.

The state of the art arcuate (crescentic) cuts are less than 180 degrees. A preferred arcuate cut of bone is equal to or greater than 180 degrees to form a stable curved-vee osteotomy.

The curved cut should not be so much greater than 180 degrees as to undercut the bone since this is unnecessary and would undermine the osteotomy's strength.

Figure 5:
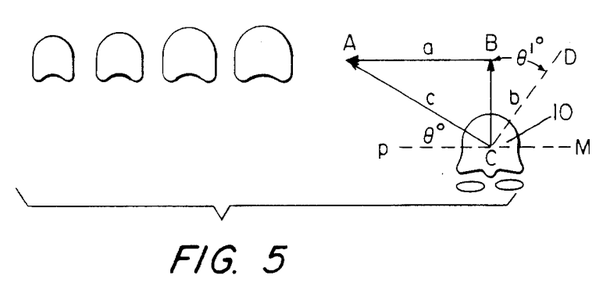
FIG. 5 is a cross-sectional view of the metatarsal bones of a foot with a particular foot deformity and showing a vector solution for repositioning the malpositioned metatarsal bone.
Figure 6:
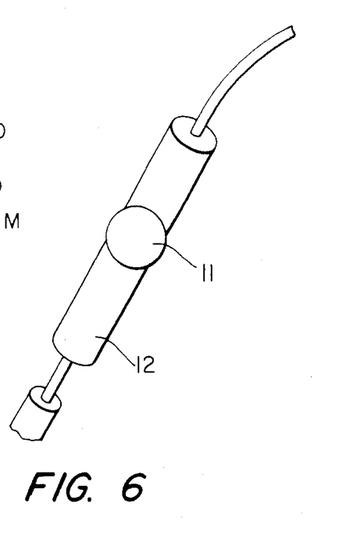
FIG. 6 is a perspective view of an oscillation saw and positional guidance means attached to same.

This application also deals with the directional guidance of bone correction in space. Since a bone has a central longitudinal axis, it can be dealt with as a line in space. It can be represented in space by directional cosines or directional numbers for both the pre-operative position and the planned post-operative position. Angular changes or corrections in bones can also be expressed in the magnitude and direction of the displacement of the bone in relation to a pivot point herein the center of rotation of the curved cut. The displacements can be treated as vectors. The three body planes, transverse, sagittal and frontal, are at right angles to each other and form axis x, y and z. Changes of bone in space are made in reference to these body planes. Hence, in FIG. 5, arrow (a) refers to an 8 degree transverse-frontal plane displacement or correction of the end, or head, of the first metatarsal (10) while arrow (b) depicts a 5 degree correction or displacement of the end or head of the first metatarsal (10) in the sagittal-frontal plane. The first metatarsal (10) at position C is to be corrected to position A. This can be accomplished by one osteotomy of an angular dimension equal to arrow (c) which computed from the Pythagorean Theorem $c^2 = a^2 + b^2$ is 9.43 degrees. This correctional movement from C to A is in all three body planes. The bone-cut guide apparatus can now be used. A wedge segment of 9.43 degrees can be made by dialing the guide slot arm cutting position linked to a computer display or directly visualized (as described in the first continuation-in-part application) or by selecting the closest individual osteoguide that can be used, e.g., a 9.5 degree osteoguide. The arcuate cut made to receive the tab of the osteoguide would be made theta prime degrees from a vertical perpendicular to the central longitudinal axis of the bone. Angle theta, and hence its equal theta prime, can be computed by the tangent vector (b)/vector (a). This system can be placed on a computer for both computation and direction. To right triangle ABC (FIG. 5) containing vector sides a, b and c can be constructed right triangle ADC forming similar triangles ABC, DBC; hence, angle BAC=angle DBC and angle BDC and angle BAC=angle BCD. Correction with the osteoguide is always in a plane at 90 degrees to the axis of the curved cut; hence, correction (c) is made at a curved cut positon C D which is theta prime degrees from the vertical B C. Theta degrees in this instance can be computed from the tangent of ⅝ or theta equals 32 degrees from the vertical BC. of bone positioning can be of much narrower parameters in some individuals. Bone size and shape often dictate surgical planning outside the normal range of parameters. To this dilemma and in the course of routine surgical planning comes the assistance of the computer-aided design techniques wherein a surgeon can use a light pen or other interactive graphic design means to attain the optimal biomechanical structure for a surgical case by computer. Direct design input by the surgeon coupled with the known parameters and the patient's particular biomechanical mensurations will yield osteoguide angulations necessary to achieve the end result.

The case data is synthesized by computer to give the information and directional guidance to the osteoguide system as described above. In similar fashion in a given surgical case, the computer, when given relative length of hand or foot bones and the precise angulation of the axes of the bone lengths one to the other, can give a graphic printing of these bones. In like manner, the computer can be programmed to be given a radiograph or bone tracing for computation of the central bony axes and relative angulations.

If the surgeon desires a wedge removal of a predetermined number of degrees, a template of such a wedge and the corrective result of either the curved-vee osteotomy or the traditional pie-shaped variety can be graphically made from the above information. If the surgeon is not sure of the angular correction needed, and hence does not furnish the wedge size data, a template can still be made on the basis of the bone length and relative angulation data furnished for the first graphic printout cited in the previous paragraph.

From the foregoing description, one skilled in the art can easily ascertain the essential characteristics of this invention and without departing from the spirit and scope thereof can make various changes and modifications of the invention to adopt to its various diagnostic and surgical uses.

I claim:

1. Osteotomy guide apparatus comprising an arcuate tab section, a guide body disposed on said tab section, a guide arm extending from said guide body with a guide slot positioned therein, means on said tab section cooperating with means on said guide body for adjustably positioning one relative to the other.

2. The osteotomy guide apparatus of claim 1 wherein said arcuate tab section is comprised of a base having an arcuate tab positioned on one side thereof and the first mentioned means on the other side thereof and being comprised of an upstanding projection, said projection adapted to be positioned within an opening provided in said guide body.

3. The osteotomy guide apparatus of claim 2 wherein the guide arm extends at an angle from said guide body.

4. The osteotomy guide apparatus of claim 3 wherein said guide arm and slot therein are disposed in a curvilinear plane with respect to said guide body.

5. The osteotomy guide apparatus of claim 3 wherein a second guide arm with slot extends from said guide body and is positioned opposite said first arm.

6. The osteotomy guide apparatus of claim 3 wherein said guide slot includes a substantially "V" shaped portion.

7. The osteotomy guide apparatus of claim 2 wherein a removable fastener is disposed within said projection and opening for securing said arcuate tab section and said guide body to one another.

8. The osteotomy guide apparatus of claim 1, wherein said guide arm is angularly disposed toward the cross sectional curvature of the bone, whereby the same may conform to the sectional curvature of the bone to facilitate straight cuts thereof.

9. The osteotomy guide apparatus comprising a one piece body having at least a pair of arcuate tabs disposed on either side of the body, as mirror images of each other, a guide arm extending outwardly from said body and having a guide slot formed therein; said slot beginning at the outward edge of said guide arm and extending inwardly past and adjacent to the ends of said arcuate tabs to a point within said body, said slot being angularly disposed to the radius of said arcuate tabs, said slot being a single continuous slot passing entirely through said arm, a second pair of tabs planar in shape on either side of said guide arm, each a mirror image of each other, both planar tabs disposed at the same angle to a radius of said arcuate tabs, both planar tabs at a specific angular dimension from said slot, whereby said apparatus can be used for making left and right bone wedges.

10. The osteotomy guide apparatus of claim 9 wherein said guide arm is angularly disposed downwardly of said body whereby the same may conform to the sectional curvature of the bone to facilitate straight cuts thereof.

11. The osteotomy guide apparatus of claim 9 wherein said second pair of planar tabs are each positioned on a pivot member, said member rotating on an axis through the center of the arc of the arcuate tabs, said pivot member allowing said planar tabs to be adjustably rotated from said slot thereby changing the angular dimension between said slot and said tabs to yield different size bone wedges.

12. The osteotomy guide apparatus of claim 11 wherein scale means are provided on said body to assist in positioning said second pair of tabs.

13. The osteotomy guide apparatus of claim 9 wherein a second slot is formed in said guide arm and the second pair of tabs comprises a single planar sheet disposed therein with portions thereof extending outwardly of said second slot.

14. The osteotomy guide apparatus of claim 13 wherein said planar sheet is generally of a trapezoidal shape and has a notch portion removed from the central portion of the major base thereof, said notch being sized and configured in such fashion that the sides of the notch are in bearing engagement with said arm when said planar sheet is inserted in said second slot.

15. The osteotomy guide apparatus of claim 9 in combination with a guide holder comprising handle means culminating in an arcuate housing adapted to engage an osteotomy guide apparatus, said arcuate housing containing an opening therein through which the osteotomy guide arm extends and engages, whereby the arcuate tab can be rotated to the end of an arcuate cut.

16. The osteotomy method comprising the steps of making an arcuate cut through one side of a bone, making a planar cut through a side of the bone opposite the side with the arcuate cut and extending the planar cut from the arcuate cut to the said opposite side of the bone at an angle to the radius of the arcuate cut, making a third cut at the same angle to a second radius of the arcuate cut which radius is offset the desired angular displacement from the second cut thus yielding a bony wedge.

* * * * *